(12) United States Patent
Lebner

(10) Patent No.: US 12,076,016 B2
(45) Date of Patent: Sep. 3, 2024

(54) WOUND CLOSURE DEVICE

(71) Applicant: Jeffrey Lebner, Boca Raton, FL (US)

(72) Inventor: Jeffrey Lebner, Boca Raton, FL (US)

(73) Assignee: Sutura Industries LLC, Boca Raton, FL (US)

( * ) Notice: Subject to any disclaimer, the term of this patent is extended or adjusted under 35 U.S.C. 154(b) by 215 days.

(21) Appl. No.: 17/137,532

(22) Filed: Dec. 30, 2020

(65) Prior Publication Data

US 2021/0196274 A1   Jul. 1, 2021

Related U.S. Application Data

(60) Provisional application No. 62/955,023, filed on Dec. 30, 2019.

(51) Int. Cl.
*A61B 17/08*    (2006.01)
*A61B 17/00*    (2006.01)

(52) U.S. Cl.
CPC .......... *A61B 17/085* (2013.01); *A61B 17/083* (2013.01); *A61B 2017/00889* (2013.01); *A61B 2017/00951* (2013.01); *A61B 2017/086* (2013.01)

(58) Field of Classification Search
CPC ................ A61B 17/085; A61B 17/083; A61B 2017/00889; A61B 2017/00951; A61B 2017/086; A61F 13/00; A61F 2013/00089; A61F 2013/00106; A61F 13/00051; A61F 2013/00361; A61F 2013/00451; A61F 2013/00544; A61F 13/02
See application file for complete search history.

(56) References Cited

U.S. PATENT DOCUMENTS

| | | | |
|---|---|---|---|
| 5,534,010 A * | 7/1996 | Peterson | A61B 17/085 606/215 |
| 6,329,564 B1 | 12/2001 | Lebner | |
| 6,822,133 B2 | 11/2004 | Lebner | |
| 6,831,205 B2 | 12/2004 | Lebner | |
| 7,332,641 B2 | 2/2008 | Lebner et al. | |
| 7,354,446 B2 | 4/2008 | Lebner | |
| 7,414,168 B2 | 8/2008 | Lebner | |
| 7,511,185 B2 | 3/2009 | Lebner | |
| 7,838,718 B2 | 11/2010 | Lebner | |
| 8,105,353 B2 | 1/2012 | Lebner et al. | |
| 8,636,763 B2 | 1/2014 | Lebner | |
| 2003/0092969 A1* | 5/2003 | O'Malley | A61B 17/02 600/216 |

(Continued)

*Primary Examiner* — Tan-Uyen T Ho
*Assistant Examiner* — David P Stein
(74) *Attorney, Agent, or Firm* — Nolan IP Law; Jason M. Nolan

(57) ABSTRACT

A device and method for closing a wound is provided. The device includes an anchoring pad having a bottom surface and an opposing top surface, such that the bottom surface is configured to adhere to a first side of the wound; a complementary pad having a bottom surface and an opposing top surface, such that the bottom surface is configured to adhere to a second side of the wound; and a pull tab having a bottom surface and an opposing top surface, such that the top surface is configured to adhere to the complementary pad and/or the second side of the wound, and the pull tab is coupled to the complementary pad by at least one connecting strap that is slidably connected to the anchoring pad.

10 Claims, 7 Drawing Sheets

(56) References Cited

U.S. PATENT DOCUMENTS

| | | | |
|---|---|---|---|
| 2011/0017633 A1* | 1/2011 | Holstein | A61F 17/00 206/570 |
| 2014/0171849 A1* | 6/2014 | Fischell | A61F 13/0246 602/53 |
| 2015/0051530 A1* | 2/2015 | Noda | A61B 17/085 602/41 |
| 2016/0249924 A1* | 9/2016 | Belson | A61B 17/0466 606/216 |
| 2017/0035422 A1* | 2/2017 | Belson | A61B 17/085 |

* cited by examiner

WOUND CLOSURE DEVICE

RELATED AND CO-PENDING APPLICATION

This application claims the benefit of priority under 35 U.S.C. § 119(e) of U.S. Provisional Application Ser. No. 62/955,023 filed on Dec. 30, 2019, the content of which is relied upon and incorporated herein by reference in its entirety.

FIELD

The disclosure generally relates to a device for closing wounds, including lacerations and incisions, and more particularly to a device for closing wounds that is operable by a user having a wound and a single dexterous hand available for tending to the wound.

BACKGROUND

Wounds are generally closed with sutures, staples, and clamps, etc. These devices generally require a wounded person to seek assistance from another person, including a medical professional at a hospital or medical facility. For at least these reasons, there is a need for a wound closure device that can be operated by the person having the wound when assistance is not available.

SUMMARY

In various embodiments, a device for closing a wound is provided. The device can include an anchoring pad comprising a bottom surface and an opposing top surface, wherein the bottom surface is configured to adhere to a first side of the wound; a complementary pad having a bottom surface and an opposing top surface, wherein the bottom surface is configured to adhere to a second side of the wound; and a pull tab having a bottom surface and an opposing top surface, wherein the top surface is configured to adhere to the complementary pad and/or the second side of the wound, wherein the pull tab is coupled to the complementary pad by at least one connecting strap that is slidably connected to the anchoring pad.

In various embodiments, a kit comprising the device is provided. The kit can further include an antiseptic and an antibiotic.

In various embodiments, a method of closing a wound is provided. The method can include providing a device for closing the wound. The device can include an anchoring pad comprising a bottom surface and an opposing top surface, wherein the bottom surface is configured to adhere to a first side of the wound; a complementary pad having a bottom surface and an opposing top surface, wherein the bottom surface is configured to adhere to a second side of the wound; and a pull tab having a bottom surface and an opposing top surface, wherein the top surface is configured to adhere to the complementary pad and/or the second side of the wound, wherein the pull tab is coupled to the complementary pad by at least one connecting strap that is slidably connected to the anchoring pad. The method can further include attaching the anchoring pad and complementary pad to opposite sides of the wound; pulling the pull tab to move the complementary pad closer to the anchoring pad; and adhering the pull tab to the complementary pad.

It is to be understood that both the foregoing general description and the following detailed description describe various embodiments and are intended to provide an overview or framework for understanding the nature and character of the claimed subject matter. The accompanying drawings are included to provide a further understanding of the various embodiments and are incorporated into and constitute a part of this specification. The drawings illustrate the various embodiments described herein and, together with the description, explain the principles and operations of the claimed subject matter.

BRIEF DESCRIPTION OF THE DRAWINGS

A complete understanding of the present embodiments and the advantages and features thereof will be more readily understood by reference to the following detailed description, appended claims, and accompanying drawings, wherein:

Figure 1:
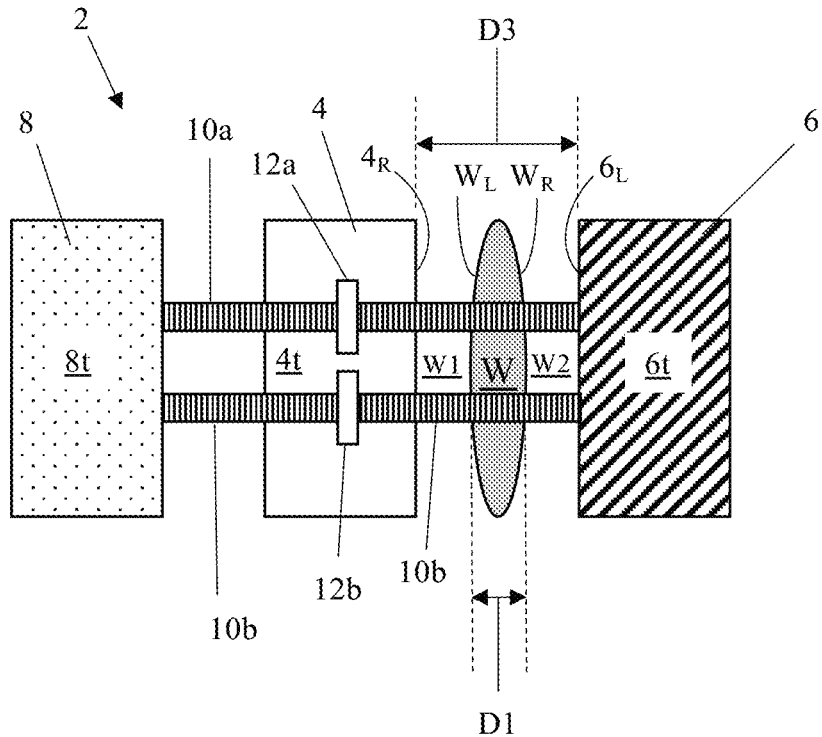
FIG. 1 is a top view of a wound-closing device in an open position and a wound shown between the anchoring pad and complementary pad, in accordance with some embodiments described herein.

The drawings are not necessarily to scale, and certain features and certain views of the drawings may be shown exaggerated in scale or in schematic in the interest of clarity and conciseness.

DETAILED DESCRIPTION

Reference will now be made in detail to the exemplary embodiment(s), examples of which is/are illustrated in the accompanying drawings. Whenever possible, the same reference characters will be used throughout the drawings to refer to the same or like parts.

Before describing the exemplary embodiments, it is noted the embodiments reside primarily in combinations of components and procedures related to the apparatus. Accordingly, the apparatus components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

The specific details of the various embodiments described herein are used for demonstration purposes only, and no unnecessary limitation or inferences are to be understood therefrom. Furthermore, as used herein, relational terms, such as "first" and "second," "top" and "bottom," and the like, may be used solely to distinguish one entity or element from another entity or element without necessarily requiring or implying any physical or logical relationship, or order between such entities or elements.

In various embodiments, a device 2 for closing a wound W is provided. As shown in FIGS. 1-10B, in some embodiments the device 2 comprises an anchoring pad 4, a complementary pad 6, and a pull tab 8 coupled to the complementary pad 6 through a connecting strap 10. In some embodiments, the connecting strap 10 comprises a plurality of strips. For example, in FIGS. 1, 2, and 4B, the connecting strap 10 comprises connecting strips 10a, 10b. In some embodiments, the connecting strap 10 is slidably connected to the anchoring pad 4. In such embodiments, the anchoring pad 4 comprises an opening (e.g., slit) or loop 12 or a plurality of openings (e.g., slits) or loops 12a, 12b, as shown in FIGS. 1-10B.

In some embodiments, the anchoring pad 4 is adapted to adhere to the skin of a subject at a position on a first side W1 of the wound W and the complementary pad 6 is adapted to adhere to a position on a second side W2 of the wound W. In such embodiments, the anchoring pad 4 comprises a bottom surface 4b and an opposing top surface 4t, wherein the bottom surface 4b is adapted to adhere to the first side W1 of the wound W such that the right side $4_R$ of the anchoring pad 4 is positioned near to the left edge $W_L$ of the wound W. In such embodiments, the complementary pad 6 comprises a bottom surface 6b and an opposing top surface 6t, wherein the bottom surface 6b is adapted to adhere to the second side W2 of the wound W such that the left side $6_L$ of the complementary pad 6 is positioned near to the right edge $W_R$ of the wound W. In such embodiments, the pull tab 8 comprises a bottom surface 8b and an opposing top surface 8t.

Figure 2:
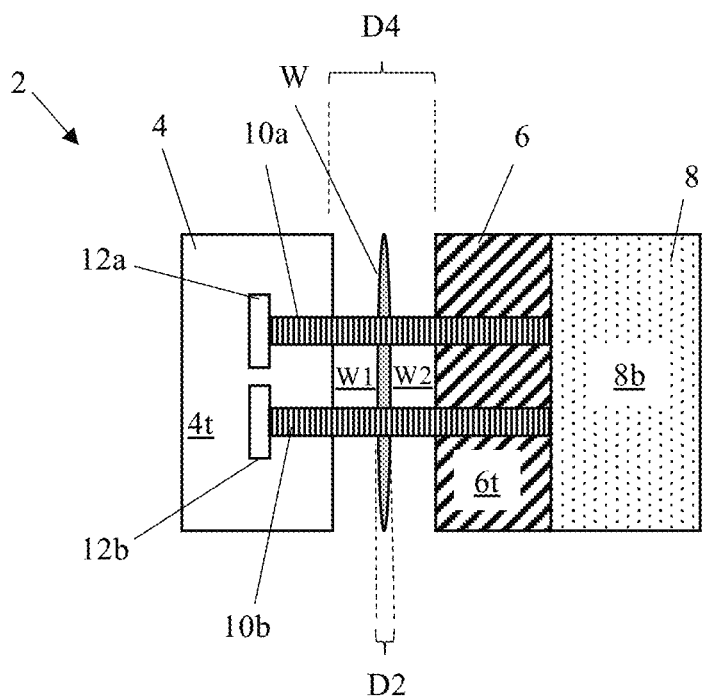
FIG. 2 is a top view of the wound-closing device in a closed position, with the pull tab pulled over onto the complementary pad, in accordance with FIG. 1.

In some embodiments, the pull tab 8 is moveable from an open position, as shown in FIG. 1, to a closed position, as shown in FIG. 2. In the closed position, the top surface 8t of the pull tab 8 adheres to the top surface 6t of the complementary pad 6 and/or the tissue (e.g., skin) on the second side W2 of the wound W. In some embodiments, when the pull tab 8 is in the open position, the top surface 8t of the pull tab faces away from the wound W and surrounding tissue. In the open position, the opposing sides W1, W2 of the wound W are separated by a first distance D1, as shown in FIG. 1. In such embodiments, when the pull tab 8 is in the closed position, the top surface 8t of the pull tab faces toward the tissue or skin that comprising the wound W and the opposing edges $W_L$, $W_R$ of the wound W are separated by a second distance D2, as shown in FIG. 2. In such embodiments, the first distance D1 is greater than the second distance D2. In some embodiments, the second distance D2 is so small that the opposing edges $W_L$, $W_R$ of the wound W appear to be touching one another.

In some embodiments, when the pull tab 8 is in the open position, the right side $4_R$ of the anchoring pad 4 and the left side $6_L$ of the complementary pad 6 are separated by a third distance D3. In such embodiments, when the pull tab 8 is in the closed position, the right side $4_R$ of the anchoring pad 4 and the left side $6_L$ of the complementary pad 6 are separated by a fourth distance D4. In some embodiments, the third distance D3 is the substantially the same as the fourth distance D4. In some embodiments, the third distance D3 is greater than the fourth distance D4.

Figure 3A:
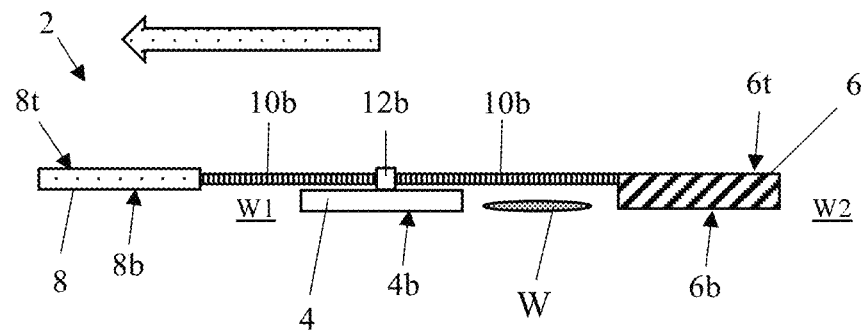
FIG. 3A is side view of the wound-closing device in an open position, as the pull tab is pulled away from the anchoring pad, in accordance with FIG. 1.
Figure 3B:
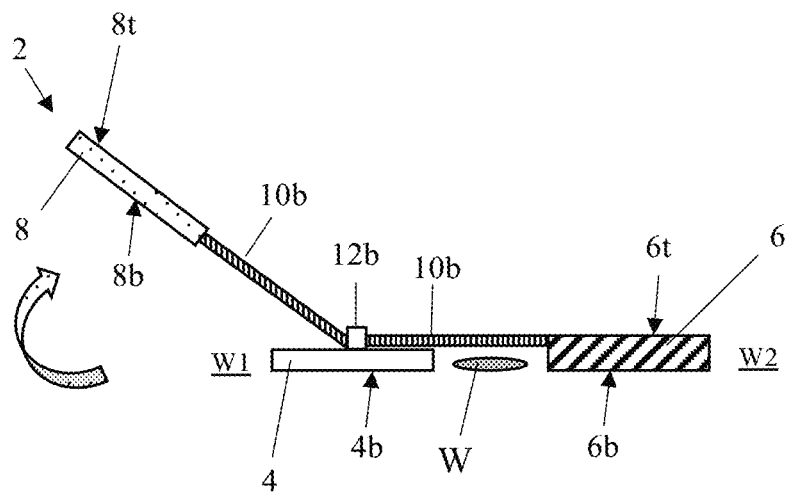
FIG. 3B is a side view of the wound-closing device in an open position as the pull tab is pulled up from the anchoring pad, in accordance with FIG. 1.
Figure 3C:
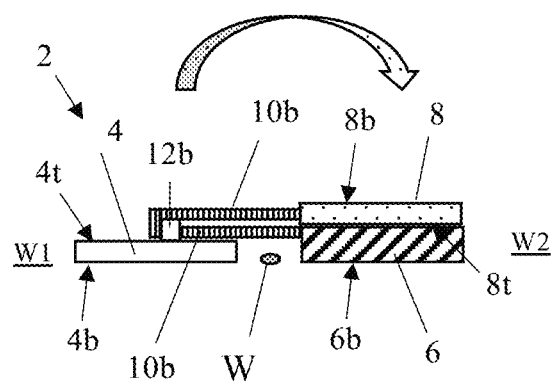
FIG. 3C is a side view of the wound-closing device in the closed position, with the pull tab pulled over and adhered to the complementary pad, in accordance with FIG. 2.

FIGS. 3A-3C show side views of the device 2 and, in particular, the pull tab 8 moving from an open position to a closed position. FIG. 3A shows the pull tab 8 pulled laterally away from the anchoring pad 4 after the bottom surface 4b of the anchoring pad 4 and the bottom surface 6b of the complementary pad 6 have been placed and adhered to the skin of a patient. In such embodiments, the anchoring pad 4 is on the first side W1 of the wound W and the complementary pad 6 is on the second side W2 of the wound W.

FIG. 3B shows the pull tab 8 being moved toward the closed position. In some embodiments, as shown in FIG. 3B, when the pull tab 8 is pulled up, the connecting strips 10a, 10b slide through the loops 12a, 12b. In such embodiments, the opposing edges $W_L$, $W_R$ of the wound W are forced together as the pull tab 8 is pulled out and up from the first side W1 of the wound W and pulled over the wound W toward the second side W2 of the wound W. The wound W closes as the pull tab 8 is pulled toward the complementary pad 6 and the opposing edges $W_L$, $W_R$ of the wound W are forced toward one another.

FIG. 3C shows the pull tab 8 in the closed position. In some embodiments, as shown in FIG. 3C, the top surface 8t of the pull tab is adhered to the top surface 6t of the complementary pad 6 and/or the tissue or skin of the patient on the second side W2 of the wound W. In such embodiments, the connecting strips 10a, 10b slide through the openings 12a, 12b and are then folded down toward the wound W. In such embodiments, the anchoring pad 4 and the complementary pad 6 are compressed toward one another until the first and second sides W1, W2 of the would W are touching, substantially touching, or as close to one another as reasonably expected (depending on the size, shape, and seriousness of the wound).

Figure 4A:
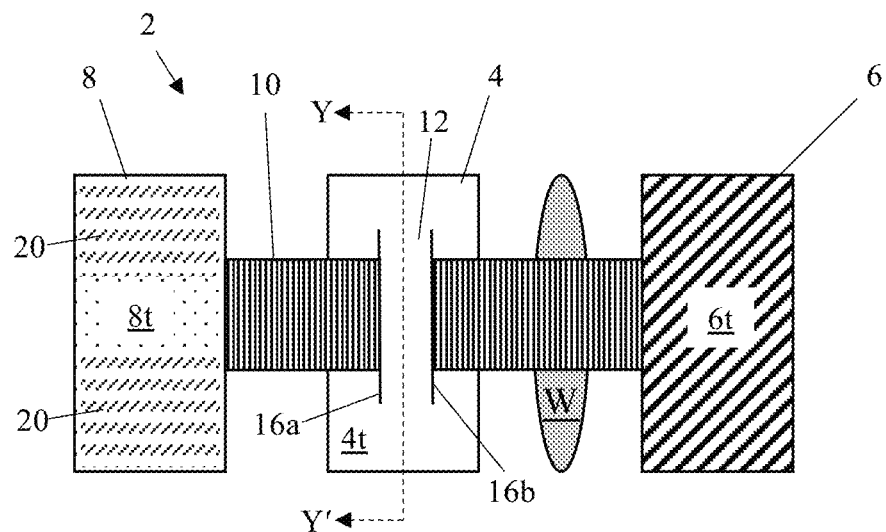
FIG. 4A is a top view of the wound-closing device showing an alternative arrangement of the anchoring pad, in accordance with FIG. 1.

In some embodiments, as shown in FIG. 4A, the connecting strap 10 is a single strip. In FIG. 4A, the anchoring pad 4 comprises two slits 16a, 16b which create a loop 12 on the top surface 4t. In such embodiments, the connecting strap 10 slides from the complementary pad 6 through the opening 16b, passes under the loop 12 and through the opening 16a toward the pull tab 8.

Figure 4B:
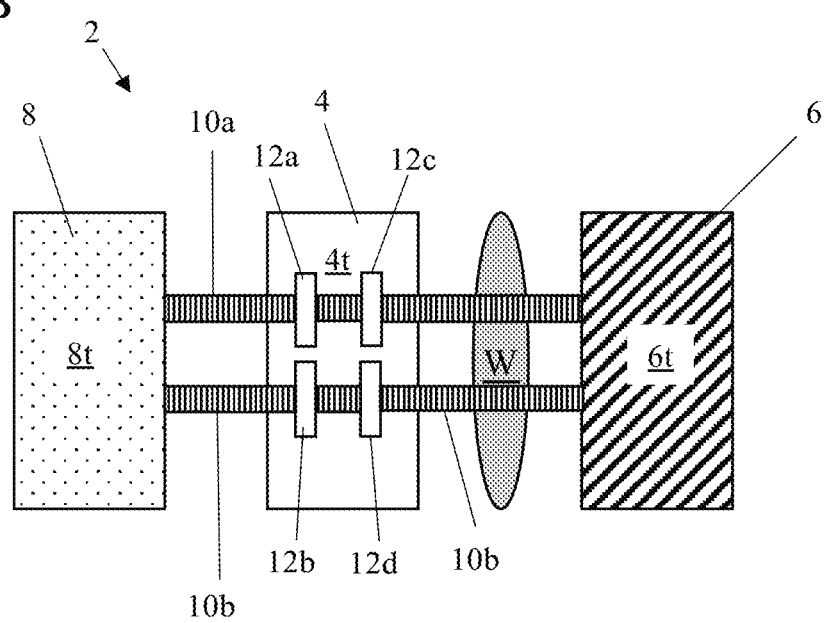
FIG. 4B is a partial top view of the wound-closing device showing an alternative arrangement of the anchoring pad, in accordance with FIG. 1.

In some embodiments, as shown in FIG. 4B, the connecting strap 10 comprises a plurality of strips 10a, 10b. In some embodiments, as shown in FIG. 1, the anchoring pad 4 comprises a loop 12a, 12b for each strip 10a, 10b. In other embodiments, as shown in FIG. 4B, the anchoring pad 4 comprises a plurality of loops 12a, 12c and 12b, 12d for each strip 10a, 10b. In such embodiments, the loops may be arranged in a grid comprising at least two rows of loops 12a and 12c; 12b and 12d and at least two columns of loops 12a and 12b; 12c and 12d. In such embodiments, the strips 10a, 10b are slidable connected to the complementary pad 6 and the pull tab 8, and pass slidably through the loops 12a, 12c and 12b, 12d.

Figure 6:
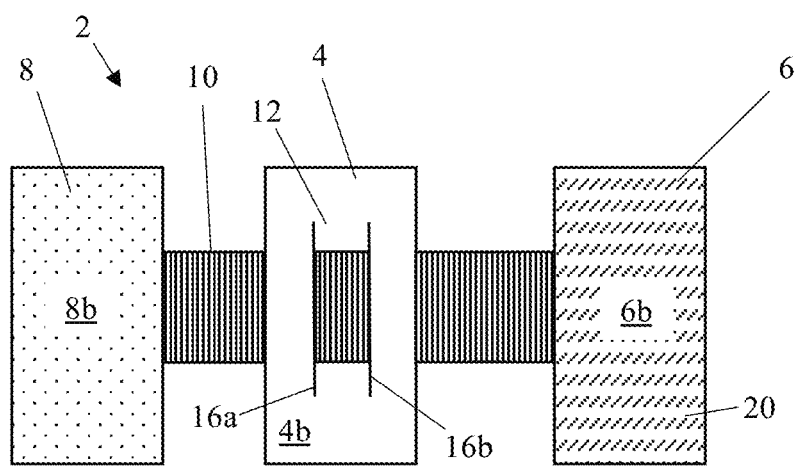
FIG. 6 is a bottom view of the wound-closing device according to FIG. 4A.
Figure 7:
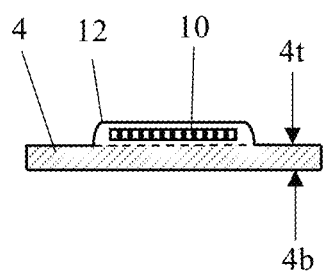
FIG. 7 is a cross-sectional view of the wound-closing device through the Y-Y' line in FIG. 4A.
Figure 8:
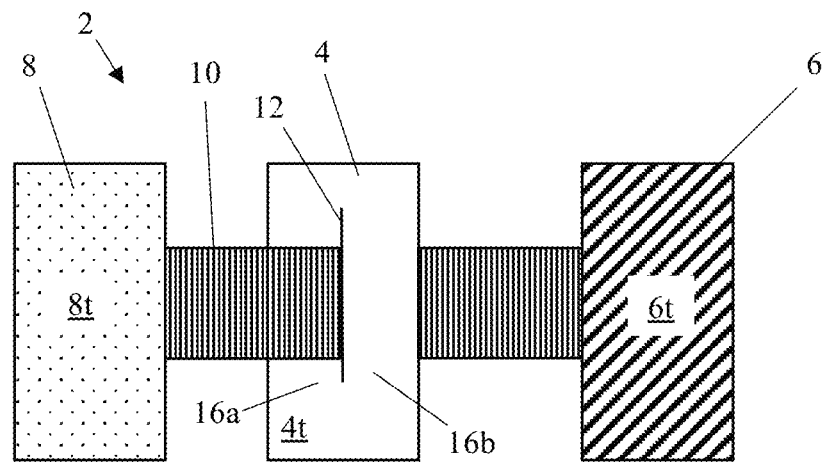
FIG. 8 is a top view of the wound-closing device in an open position, in accordance with some embodiments described herein.

In some embodiments, the loop 12 or plurality of loops 12a, 12b in the anchoring pad 4 are connected to the top surface 4t of the anchoring pad 4, as shown in FIG. 1. In some embodiments, the loop 12 is formed by two parallel slits cut into the top surface 4t of the anchoring pad 4. For example, the device 2 in FIG. 4A comprises a loop 12 formed with two openings (slits) in the anchoring pad 4. In such embodiments, the slits are long enough to receive the connecting strap 10 and to allow the connecting strap 10 to slide through. FIG. 6 shows a bottom view of the device 2 in FIG. 4A with the connecting strap 10 visible from the bottom as it slides through the loop 12 formed by the slits 16a, 16b. FIG. 7 shows a cross-sectional view of the wound closing device 2 in FIG. 4A through the Y-Y' line. FIG. 7 shows the loop 12 created by the slits 16a, 16b in the anchoring pad 4, and the connecting strap 10 passes through the loop 12.

In some embodiments, adhesive 20 is applied to the bottom surface 4b of the anchoring pad 4, the bottom surface 6b of the complementary pad 6, and the top surface 8t of the pull tab 8. As such, the anchoring pad 4 and the complementary pad 6 are adapted to adhere to the skin of the patient on the first and second sides W1, W2 of the wound W on a subject, and the top surface 8t of the pull tab 8 is adapted to adhere to the top surface 6t of the complementary pad 6 and/or the skin of the patient on the second side W2 of the wound.

Figure 5A:
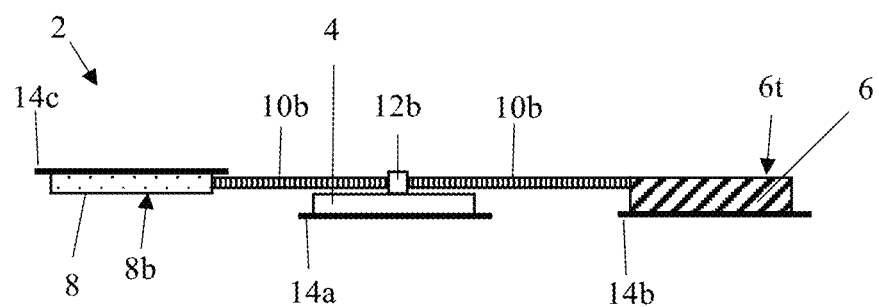
FIG. 5A is a side view of the wound-closing device with peel strips on the top side of the pull tab and the bottom side of each of the anchoring and complementary pads, in accordance with FIG. 1.
Figure 5B:
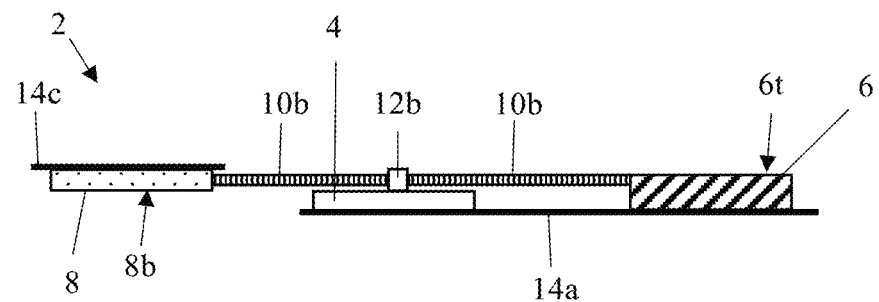
FIG. 5B is a side view of the wound-closing device with peel strips on the top side of the pull tab and the bottom side of the anchoring and complementary pads, in accordance with FIG. 1.

In some embodiments, as shown in FIGS. 5A and 5B, the device 2 further comprises a removable peel strip 14 or plurality of removable peel strips 14a, 14b, 14c covering the adhesive on the bottom surface 4b of the anchoring pad 4, the bottom surface 6b of the complementary pad 6, and the top surface 8t of the pull tab 8. In some embodiments, as shown in FIG. 5A, there is a single peel strip 14a covering the bottom surface 4b of the anchoring pad 4 and the bottom surface 6b of the complementary pad 6. In some embodiments, as shown in FIG. 5B, there are separate peel strips 14a, 14b covering each of the bottom surface 4b of the anchoring pad 4 and the bottom surface 6b of the complementary pad 6. In some embodiments, the peel strip(s) 14 is a peelable film.

Figure 9:
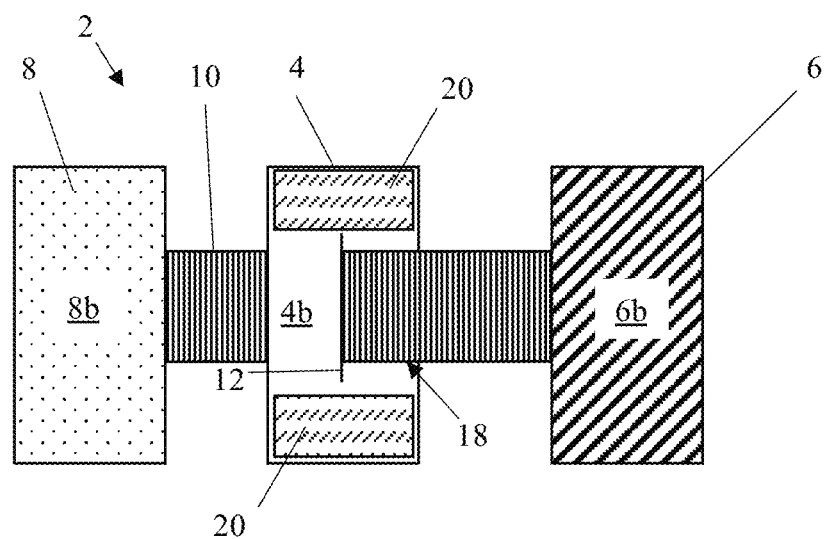
FIG. 9 is a bottom view of the wound-closing device in FIG. 7.
Figure 10A:
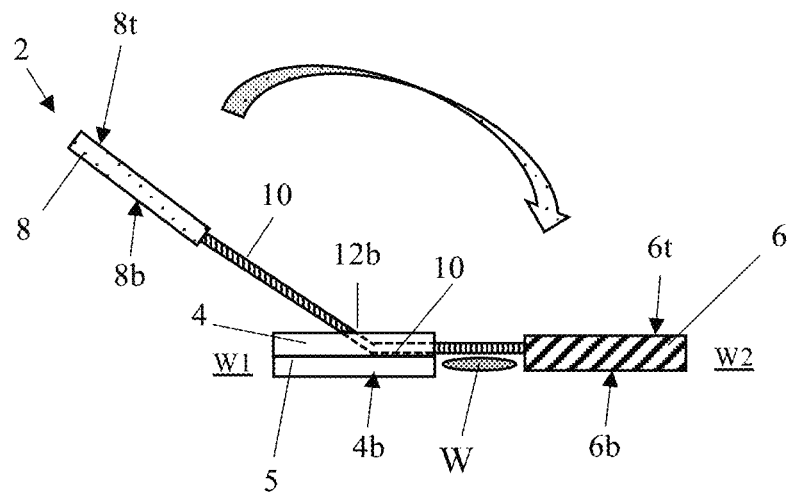
FIG. 10A is a side view of a wound-closing device with a two-layer anchoring pad in the open position, in accordance with some embodiments described herein.
Figure 10B:
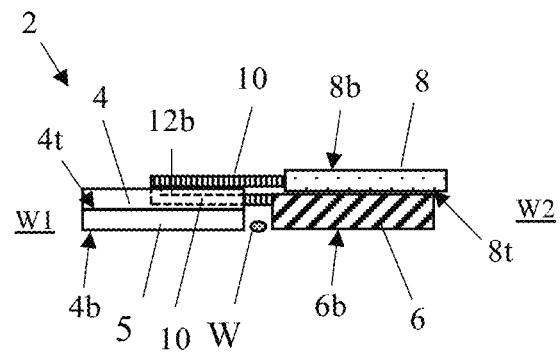
FIG. 10B is a side view of the wound-closing device in FIG. 9A with the pull tab in the closed position.

In some embodiments, the wound closing device 2 comprises an anchoring pad 4 with a single opening (e.g., slit) 12. For example, as shown in the top view in FIG. 8, the connecting strap 10 connecting the complementary pad 6 and the pull tab 8 slides through the single opening 12. In FIG. 9, the bottom view of device 2 also shows the connecting strap 10 passing through the opening 12. In some embodiments, adhesive can be applied to portions of the bottom surface 4b that do not contact the connecting strap 10, as shown in FIG. 9. In such embodiments, the bottom surface 4b includes adhesive zones 20 for adhering the anchoring pad 4 to the subject.

In some embodiments, the wound-closing device 2 comprises an anchoring pad 4 with a plurality of layers. For example, in FIGS. 10A and 10B, the device 2 is configured with an upper anchoring layer 4 and a lower anchoring layer 5. In such embodiments, the connecting strap 10 passes through a single opening, as provided in FIGS. 8 and 9, and can be pulled out, up, and then back toward the complementary pad 6. In such embodiments, the connecting strap 10 is positioned between the anchoring layers 4, 5 in a portion of the layers having no adhesive.

In various embodiments, a kit is provided. In some embodiments, the kit comprises the wound-closing device 2. In some embodiments, the kit further comprises an antiseptic and an antibiotic. In some embodiments, the antiseptic is an alcohol wipe and the antibiotic is an ointment. Other components are contemplated.

In various embodiments, a method of closing a wound is provided. In some embodiments, the method comprises providing a wound-closing device as described herein to a subject in need thereof (i.e., a subject with a wound W). In some embodiments, the method comprises attaching each of the anchoring pad 4 and the complementary pad 6 to opposite sides W1, W2 of the wound W; and pulling the pull tab 8 laterally outward, upward, and back toward the complementary pad 6 to force the opposing edges $W_L$, $W_R$ of the wound W toward one another. In some embodiments, the method further comprises adhering the pull tab 8 to the complementary pad 6 to maintain a closed or substantially-closed wound W. In some embodiments, as the pull tab 8 is pulled, the complementary pad 6 moves closer to the anchoring pad 4 while the wound W closes.

The wound-closing device 2 provided in the present disclosure has several advantages over existing products. For example, the wound-closing device 2 comprises a limited number of components and is easy to use. When a person obtains a wound to their skin, e.g., a laceration or incision, the person often has access to a medical professional who can assist in closing the wound. But when a person is alone in a remote location, for example, assistance may not be possible, and the person will have to take care of the wound on their own. Such a situation is harder if the wound is located on the person's arm because the person will only have the other arm available for applying medical treatment to the wound. In such a situation, the wound-closing device 2 provided in the present disclosure is advantageous because it can be self-applied using one hand. For example, the adhesive on the bottom surface 4b of the anchoring pad 4 can be exposed by removing the peel strip 14a, and then adhered to a first side W1 of the wound. The device 2 is now secured to the skin of the wounded person. The person can next remove the peel strip 14b on the bottom surface 6b of the complementary pad 6 and adhere the same to a second side W2 of the wound W. After both the anchoring pad 4 and complementary pad 6 are adhered to the first and second sides W1, W2 of the wound W, the person can remove the peel strip 14c on the pull tab 8, pull the pull tab 8 laterally outward so the connecting strap 10 slides through the opening 12, pull the pull tab 8 upward to further close the opposing edges $W_L$, $W_R$ of the wound W together, and then pull the pull tab 8 toward the top surface 6t of the complementary pad 6. Finally, the pull tab 8 is adhered to the complementary pad 6 and/or skin or tissue of the person on the second side W2 of the wound W.

In various embodiments, a method of stretching skin with a wound-closing device described herein is disclosed. In some embodiments, the method comprises providing a wound-closing device as described herein to a subject in need thereof. In some embodiments, the method comprises attaching each of the anchoring pad 4 and the complementary pad 6 to the tissue that needs to be stretched. In some embodiments, the tissue is on opposite sides W1, W2 of a wound W. In some embodiments, the tissue is on opposite sides of an opening resulting from a surgical procedure or injury. For example, a large opening in the skin may be required during surgery to access organs or other internal body components, and the skin will need to be stretched before it is possible to close the opening when the surgery is complete. Other examples include injuries such as skin punctures, cuts, or tears, that leave an open wound on the skin tissue of a subject. In some embodiments, the method further comprises pulling the pull tab 8 laterally outward, upward, and back toward the complementary pad 6 to force the opposing edges $W_L$, $W_R$ of the wound W or skin opening toward one another. In some embodiments, the method further comprises adhering the pull tab 8 to the complementary pad 6 so that a pulling force is constantly applied to the opposing sides of the skin. In some embodiments, as the skin stretches, the pull tab 8 can be released, retightened, and re-adhered to the complementary pad 6 to further stretch the skin. Alternatively, the device can be replaced with a new device, and the process can be repeated as needed.

Exemplary embodiments of the systems and methods are described above in detail. The systems and methods are not limited to the specific embodiments described herein, but rather, components of the systems and/or steps of the method may be utilized independently and separately from other components and/or steps described herein. For example, the system may also be used in combination with other systems and methods, and is not limited to practice with only a system as described herein. Rather, the exemplary embodiment can be implemented and utilized in connection with many other systems.

Although specific features of the present embodiments may be shown in some drawings and not in others, this is for convenience only. In accordance with the principles of the disclosure, any feature of a drawing may be referenced and/or claimed in combination with any feature of any other drawing.

This written description uses examples to disclose the present embodiments, including the best mode, and also to enable any person skilled in the art to practice the present embodiments, including making and using any devices or systems and performing any incorporated methods. The patentable scope of the present embodiments is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A device for closing a wound, comprising:
   an anchoring pad comprising a bottom surface and an opposing top surface, wherein the bottom surface is configured to adhere to a first side of the wound;
   a complementary pad comprising a bottom surface and an opposing top surface, wherein the bottom surface is configured to adhere to a second side of the wound; and
   a pull tab comprising a bottom surface and an opposing top surface, wherein the top surface is configured to adhere to the complementary pad and/or the second side of the wound,
   wherein the pull tab is coupled to the complementary pad by at least one connecting strap that is slidably connected to the anchoring pad;
   wherein the anchoring pad comprises one or more loops through which the at least one connecting strap passes; and
   wherein the one or more loops are formed on the top surface of the anchoring pad;
   wherein the one or more loops are formed by a pair of slits on the top surface of the anchoring pad;
   wherein the slits are parallel to one another and spaced apart from one another; and
   wherein the at least one connecting strap remains in contact with the top surface of the anchoring pad.

2. The device of claim 1, wherein the pull tab is moveable from an open position to a closed position,
   wherein when in the open position, the top surface of the pull tab faces away from the wound and the first and second sides of the wound are separated by a first distance,
   wherein when in the closed position, the top surface of the pull tab faces toward the wound and the first and second sides of the wound are separated by a second distance, and
   wherein the first distance is greater than the second distance.

3. The device of claim 2, wherein the anchoring pad and the complementary pad are separated by a third distance when the pull tab is in the open position, and the anchoring pad and the complementary pad are separated by a fourth distance when the pull tab is in the closed position, and wherein the third distance is greater than the fourth distance.

4. The device of claim 1, wherein the bottom surface of the anchoring pad, the bottom surface of the complementary pad, and the top surface of the pull tab comprise an adhesive.

5. The device of claim 1, further comprising at least one peel strip covering the adhesive on the bottom surface of the anchoring pad, the adhesive on the bottom surface of the complementary pad, and the adhesive on the top surface of the pull tab.

6. A device for closing a wound, comprising:
   an anchoring pad comprising a bottom surface and an opposing top surface, wherein the bottom surface is configured to adhere to a first side of the wound;
   a complementary pad comprising a bottom surface and an opposing top surface, wherein the bottom surface is configured to adhere to a second side of the wound; and
   a pull tab comprising a bottom surface and an opposing top surface, wherein the top surface is configured to adhere to the complementary pad and/or the second side of the wound,
   wherein the pull tab is coupled to the complementary pad by at least one connecting strap that is slidably connected to the anchoring pad;
   wherein the anchoring pad comprises one or more loops through which the at least one connecting strap passes; and
   wherein the one or more loops are formed on the top surface of the anchoring pad;
   wherein the one or more loops comprise a plurality of loops arranged in a grid comprising at least two rows and at least two columns;
   wherein the at least two columns includes a first column and a second column, the first column being positioned on the anchoring pad at a position that is closer to the complementary pad than the second column.

7. The device of claim 6, wherein the pull tab is moveable from an open position to a closed position,
   wherein when in the open position, the top surface of the pull tab faces away from the wound and the first and second sides of the wound are separated by a first distance,
   wherein when in the closed position, the top surface of the pull tab faces toward the wound and the first and second sides of the wound are separated by a second distance, and
   wherein the first distance is greater than the second distance.

8. The device of claim 7, wherein the anchoring pad and the complementary pad are separated by a third distance when the pull tab is in the open position, and the anchoring pad and the complementary pad are separated by a fourth distance when the pull tab is in the closed position, and
wherein the third distance is greater than the fourth distance.

9. The device of claim 6, wherein the bottom surface of the anchoring pad, the bottom surface of the complementary pad, and the top surface of the pull tab comprise an adhesive.

10. The device of claim 6, further comprising at least one peel strip covering the adhesive on the bottom surface of the anchoring pad, the adhesive on the bottom surface of the complementary pad, and the adhesive on the top surface of the pull tab.

* * * * *